US010296839B2

(12) United States Patent
Soon-Shiong

(10) Patent No.: US 10,296,839 B2
(45) Date of Patent: May 21, 2019

(54) RELATIONSHIP REASONING ENGINES

(71) Applicant: Patrick Soon-Shiong, Los Angeles, CA (US)

(72) Inventor: Patrick Soon-Shiong, Los Angeles, CA (US)

( * ) Notice: Subject to any disclaimer, the term of this patent is extended or adjusted under 35 U.S.C. 154(b) by 0 days.

(21) Appl. No.: 15/687,416

(22) Filed: Aug. 25, 2017

(65) Prior Publication Data

US 2017/0372210 A1 Dec. 28, 2017

Related U.S. Application Data

(60) Division of application No. 15/352,532, filed on Nov. 15, 2016, which is a continuation of application No. (Continued)

(51) Int. Cl.
*G06N 5/04* (2006.01)
*G06T 9/00* (2006.01)
*G16H 50/20* (2018.01)
*G06K 9/00* (2006.01)
*G06F 17/30* (2006.01)
(Continued)

(52) U.S. Cl.
CPC ........ *G06N 5/046* (2013.01); *G06F 17/3087* (2013.01); *G06F 17/30864* (2013.01); *G06F 19/00* (2013.01); *G06K 9/00624* (2013.01); *G06N 5/022* (2013.01); *G06N 5/025* (2013.01); *G06N 5/04* (2013.01); *G06N 5/041* (2013.01); *G06N 5/043* (2013.01); *G06Q 30/0241* (2013.01); *G06T 9/00* (2013.01); *G16H 50/20* (2018.01); *Y04S 10/54* (2013.01)

(58) Field of Classification Search
None
See application file for complete search history.

(56) References Cited

U.S. PATENT DOCUMENTS 4,860,213 A  8/1989  Bonissone
5,058,033 A  10/1991  Bonissone et al.
(Continued)

FOREIGN PATENT DOCUMENTS

EP  0 453 874 A2  10/1991
EP  1 672 535 A1  6/2006
(Continued)

OTHER PUBLICATIONS

Eom, S et al.; A survey of decision support system applications; Journal of the Operational Research Society (2005); pp. 1-15. (Year: 2005).*

(Continued)

*Primary Examiner* — Stanley K. Hill
(74) *Attorney, Agent, or Firm* — Mauriel Kapouytian Woods LLP; Andrew A. Noble

(57) ABSTRACT

A reasoning engine is disclosed. Contemplated reasoning engines acquire data relating to one or more aspects of various environments. Inference engines within the reasoning engines review the acquire data, historical or current, to generate one or more hypotheses about how the aspects of the environments might be correlated, if at all. The reasoning engine can attempt to validate the hypotheses through controlling acquisition of the environment data.

28 Claims, 4 Drawing Sheets

Related U.S. Application Data

14/989,724, filed on Jan. 6, 2016, now Pat. No. 9,530,100, which is a continuation of application No. 14/006,932, filed as application No. PCT/US2012/030052 on Mar. 22, 2012, now Pat. No. 9,262,719.

(60) Provisional application No. 61/466,367, filed on Mar. 22, 2011, provisional application No. 61/466,398, filed on Mar. 22, 2011.

(51) Int. Cl.
*G06N 5/02* (2006.01)
*G06Q 30/02* (2012.01)
*G06F 19/00* (2018.01)

(56) References Cited

U.S. PATENT DOCUMENTS

| | | |
|---|---|---|
| 5,119,470 A | 6/1992 | Highland et al. |
| 5,175,795 A | 12/1992 | Tsuda et al. |
| 5,412,802 A | 5/1995 | Fujinami et al. |
| 5,581,664 A | 12/1996 | Allen et al. |
| 5,706,406 A | 1/1998 | Pollock |
| 5,778,150 A | 7/1998 | Chan et al. |
| 5,930,154 A | 7/1999 | Thalhammer-Reyero |
| 6,058,206 A | 5/2000 | Kortge |
| 6,711,293 B1 | 3/2004 | Lowe |
| 7,003,433 B2 | 2/2006 | Yemini et al. |
| 7,016,532 B2 | 3/2006 | Boncyk et al. |
| 7,079,688 B1 | 7/2006 | Deco et al. |
| 7,191,163 B2 | 3/2007 | Herrera et al. |
| 7,260,501 B2 | 8/2007 | Pattipatti et al. |
| 7,337,090 B1 | 2/2008 | Yemini et al. |
| 7,418,434 B2 | 8/2008 | Barry |
| 7,447,667 B2 | 11/2008 | Gong et al. |
| 7,477,780 B2 | 1/2009 | Boncyk et al. |
| 7,548,556 B1 | 6/2009 | Wittenschlaeger |
| 7,564,469 B2 | 7/2009 | Cohen |
| 7,565,008 B2 | 7/2009 | Boncyk et al. |
| 7,603,428 B2 | 10/2009 | Wittenschlaeger |
| 7,680,324 B2 | 3/2010 | Boncyk et al. |
| 7,904,602 B2 | 3/2011 | Wittenschlaeger |
| 8,683,591 B2 | 3/2014 | Wittenschlaeger |
| 8,868,700 B2 | 10/2014 | Wittenschlaeger |
| 9,262,719 B2 | 2/2016 | Soon-Shiong |
| 9,530,100 B2 | 12/2016 | Soon-Shiong |
| 9,576,242 B2 | 2/2017 | Soon-Shiong |
| 2003/0004958 A1 | 1/2003 | Russell |
| 2004/0010733 A1 | 1/2004 | S. et al. |
| 2004/0093331 A1 | 5/2004 | Garner et al. |
| 2004/0103108 A1 | 5/2004 | Andreev et al. |
| 2006/0168195 A1 | 7/2006 | Maturana et al. |
| 2007/0136222 A1 | 6/2007 | Horvitz |
| 2009/0024553 A1 | 1/2009 | Angell et al. |
| 2009/0327811 A1 | 12/2009 | Hofford |
| 2010/0008540 A1 | 1/2010 | Shet et al. |
| 2010/0223216 A1 | 9/2010 | Eggert et al. |
| 2010/0278420 A1 | 11/2010 | Shet et al. |
| 2010/0287478 A1 | 11/2010 | Avasarala et al. |
| 2010/0312913 A1 | 12/2010 | Wittenschlaeger |
| 2011/0153362 A1 | 6/2011 | Valin et al. |
| 2011/0231356 A1 | 9/2011 | Vaidyanathan et al. |
| 2012/0143808 A1 | 6/2012 | Karins et al. |
| 2012/0149808 A1 | 6/2012 | Hajek et al. |
| 2013/0253942 A1 | 9/2013 | Liu et al. |
| 2014/0270482 A1 | 9/2014 | Chakraborty et al. |
| 2014/0289323 A1 | 9/2014 | Kutaragi et al. |
| 2017/0061303 A1 | 3/2017 | Soon-Shiong |
| 2017/0262542 A1 | 9/2017 | Soon-Shiong |

FOREIGN PATENT DOCUMENTS

| | | |
|---|---|---|
| GB | 2 278 467 A | 11/1994 |
| WO | WO 88/05574 | 7/1988 |
| WO | WO 01/69410 A1 | 9/2001 |

OTHER PUBLICATIONS

Keen, Peter G. W.; Decision Support Systems: A Research Perspective; 1980; Center for Information Systems Research—MIT; 46 pages. (Year: 1980).*
Kou, Gang et al.; Multiple criteria decision making and decision support systems—Guest editor's introduction; Elsevier; Decision Support Systems 51 (2011) 247-249. (Year: 2011).*
Shim, J. P. et al.; Past, present, and future of decision support technology; Elsevier; Decision Support Systems 33 (2002) 111-126. (Year: 2002).*
U.S. Appl. No. 15/687,419, filed Aug. 25, 2017, Soon-Shiong.
International Search Report and Written Opinion for International Application No. PCT/US2012/030052 dated Oct. 29, 2012, 9 pages.
"Programming Regret for Google: Scientists Give Computers 'Hindsight' to Anticipate the Future," Technology / Computer Sciences. http://www.physorg.com/print221905627.html, Apr. 13, 2011, 2 pages.
Karlsson et al., "The vSLAM Algorithm for Robust Localization and Mapping," Proc. of Int. Conf. on Robotics and Automation (ICRA), 2005, 6 pages.
Schmidt et al., "Distilling Free-Form Natural Laws from Experimental Data," Science, Apr. 3, 2009, vol. 324, Issue 5923, pp. 81-85.
King et al., "The Automation of Science," Science, Apr. 3, 2009, vol. 324, Issue 5923, pp. 85-89.
Examination Report issued in United Kingdom Application No. GB1316556.8 dated Sep. 26, 2018, 3 pages.
Examination Report issued in United Kingdom Application No. GB1316556.8 dated Jan. 11, 2019, 3 pages.
Examination Report issued in United Kingdom Application No. GB1316556.8 dated Jan. 29, 2019, 3 pages.

* cited by examiner

Figure 4 (Prior Art)

RELATIONSHIP REASONING ENGINES

This application is a division of U.S. application Ser. No. 15/352,532, filed Nov. 15, 2016, which is a continuation of U.S. application Ser. No. 14/989,724 (now U.S. Patent No. 9,530,100), filed Jan. 6, 2016, and is related to U.S. application Ser. No. 14/989,746 (now U.S. Patent No. 9,576,242), filed Jan. 6, 2016, both of which are continuations of U.S. application Ser. No. 14/006,932 (now U.S. Patent No. 9,262,719), which is the U.S. national stage of International (PCT) Patent Application PCT/US2012/030052, filed Mar. 22, 2012; and claims the benefit of priority to U.S. Provisional Application Ser. No. 61/466,367 and U.S. Provisional Application Ser. No. 61/466,398; both filed Mar. 22, 2011. These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

FIELD OF THE INVENTION

The field of the invention is artificial reasoning technologies.

BACKGROUND

The amount of digital data made available for analysis has grown along with the growth of computing technology and communication infrastructure. Unfortunately vast mountains of data remain unused or unviewed. Great discoveries remain hidden within such datasets.

Traditional AI techniques used to analyze data merely seek to find correlations among existing data sets. Although useful in establishing possible patterns, a person is still required to reason or infer the meaning behind the patterns. Better techniques would allow a computing infrastructure to reason or infer possible relationships among aspects of a data set and then allow for automated validation of such inferences.

Others have applied varying reasoning techniques for scientific purposes as described in the paper titled "The Automation of Science", King et al., Science 3 Apr. 2009: Vol. 324 no. 5923 pp. 85-89. King's disclosed robot successfully applied reasoning techniques to make several new discoveries.

Known techniques focus on deriving facts that can be used for other purposes. For example, European patent application publication 1 672 535 to Staron et al. titled "Distributed intelligent diagnostic scheme" file Dec. 8, 2005, describes using reasoning techniques to diagnose network issues. Further, U.S. Pat. No. 5,706,406 to Pollock titled "Architecture for an Artificial Agent that Reasons Defeasibly", filed May 22, 1995, describes reasoning that can be used to control robots, assembly lines, or as an adviser for medical diagnosis. Another example includes U.S. Pat. No. 7,003,433 to Yemini et al. titled "Apparatus and Method for Event Correlation and Problem Reporting", filed Jan. 12, 2005. Yemini describes mapping symptoms to problems through matrix-based reasoning techniques.

Others have attempted to provide inference services. For example, U.S. Pat. No. 7,191,163 to Herrera et al. titled "System and Method for Providing Inference Services", filed Apr. 18, 2003, describes inference services with respect to specified domains. Another example includes U.S. Pat. No. 7,447,667 to Gong et al. titled "Method and Knowledge Structures for Reasoning about Concepts Relations, and Rules", filed Dec. 11, 2002. Still further, U.S. patent application publication 2006/0168195 to Maturana et la. titled "Distributed Intelligent Diagnostic Scheme", filed Dec. 15, 2006, describes using inference based on logical reasoning to diagnose or reconfigure a system. Yet another example includes U.S. patent application publication 2007/0136222 to Horvitz titled "Question and Answer Architecture for Reasoning and Clarifying Intentions, Goals, and Needs from Contextual Clues and Content", filed Dec. 9, 2005. Still another example includes U.S. patent application publication 2011/0153362 to Valin et al. titled "Method and Mechanism for Identifying Protecting, Requesting, Assisting and Managing Information", filed Dec. 17, 2009.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

It has yet to be appreciated that inference or reasoning techniques can be applied to a general computing infrastructure where the infrastructure itself can function as a reasoning engine based on collected ambient data. Further, the known approaches fail to appreciate the value of providing multiple possible reasoning approaches in response to an inquiry or altering the environment to seek validation of a possible conclusion reached via the reasoning approaches.

Thus, there is still a need for reasoning engines.

SUMMARY OF THE INVENTION

The inventive subject matter provides apparatus, systems and methods in which one can utilize a reasoning engine to generate a hypothesis representing an assertion that one or more aspects of an environment might have a correlation. Reasoning engines include a data interface through which the reasoning engine can acquire environment data representing aspects of the environment. Aspects can include various modalities of data (e.g., visual, audible, tactical, etc.) or even data beyond the perception of humans. In some embodiments, data from the environment can be represented as a manageable data object capable of being transported through a networking fabric and having one or more attributes describing the object. Objects can also include recognized or identified real-world object having one or more attributes. The collected data can be aggregated at or passed through one or more inference engines configured to generate a hypothesis according to various reasoning techniques. When a hypothesis is formulated, the reasoning engine can utilize a validation module to determine validity of the hypothesis by influencing acquisition of the environment data.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWING

FIG. 4 is a prior art example of submission of an inquiry to a search engine.

DETAILED DESCRIPTION

It should be noted that while the following description is drawn to a computer/server based reasoning system, various alternative configurations are also deemed suitable and may employ various computing devices including servers, interfaces, systems, platforms, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

One should appreciate that the disclosed techniques provide many advantageous technical effects including providing a computing infrastructure capable of observing a data space and inferring possible relationships among data objects in the data space. When a hypothesis is formulated, the infrastructure generates one or more signals that can affect collection of data in the data space. For example, a reasoning engine can observe a person's behavior and generate a hypothesis regarding the person's preferences. The engine can then generate or transmit a signal to a device local to the person where the signal configures the device to collect additional data to determine the validity of the hypothesis.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously. Within the context of this document, the terms "coupled to" and "coupled with" are also used to mean "communicatively coupled with" over a network, possibly via one or more intermediary network devices (e.g., peers, switches, routers, hubs, etc.).

Figure 1:
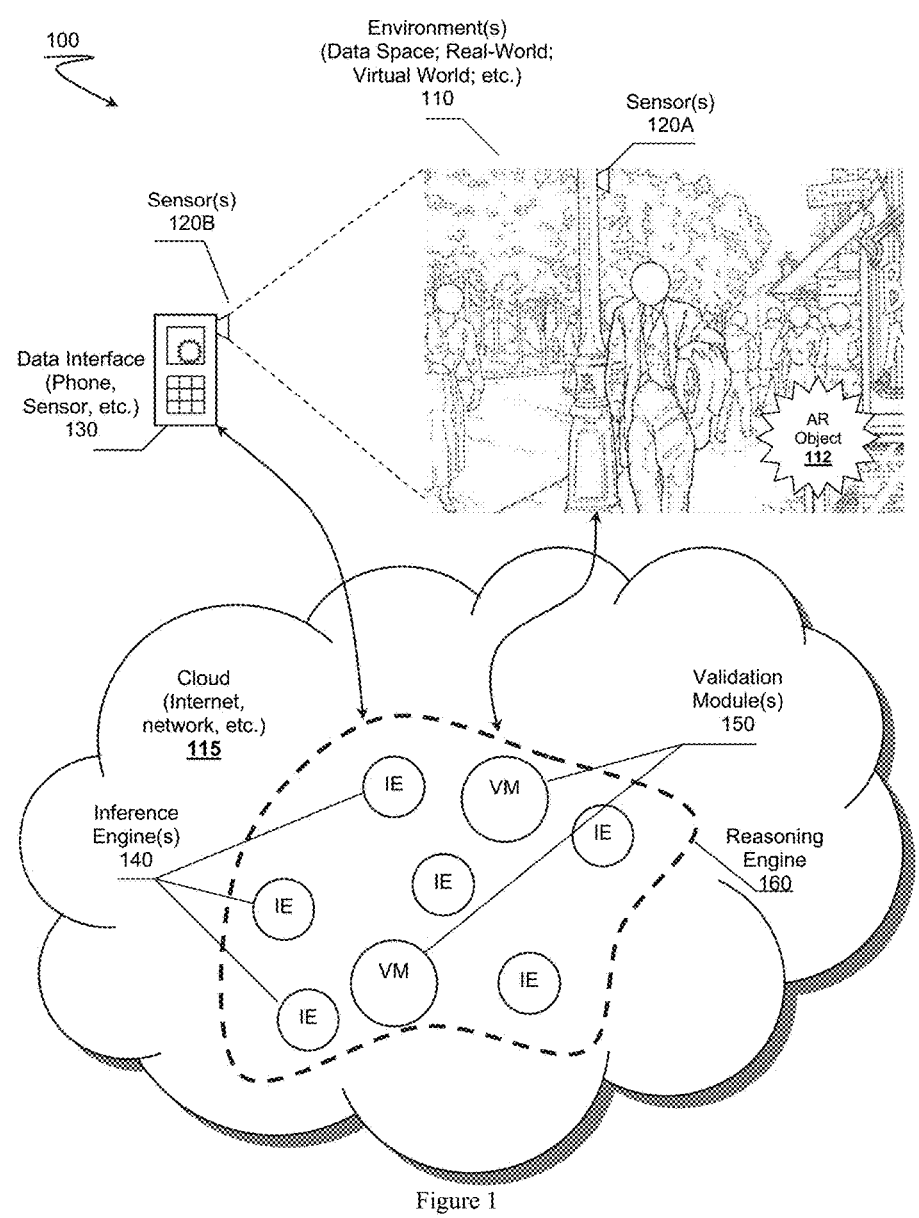
FIG. 1 is a schematic of reasoning engine environment.

FIG. 1 presents possible reasoning engine ecosystem 100 within the context of mobile phone interfacing with the reasoning engine 160 in cloud 115. Mobile phones, or other sensors 120A through 120B, capture data associated with one or more of environment 110. Inference engines 140 acquire the data and apply one or more reasoning techniques in an attempt to discover possible correlations that one would likely never have considered. Inference engine 140 can review the data, possibly in the form of manageable objects, to generate a possible hypothesis relating to how aspects of environment 110 interact or are related.

Reasoning engine 160 utilizes data interface 130 as an input/output interface to the data space represented by environment 110. Data interface 130 can take on many different forms. One preferred type of data interface 130 is a mobile computing device outfitted with one or more sensors 120B. The mobile device collects environment data relating to environment 110 local to the device. Environment data can include user identification, device usage metrics or data, sensor data, or other types of data representing aspects of the environment. Example mobile devices can include mobile phones, vehicles (e.g., trucks, cars, airplanes, spacecraft, satellites, etc.), portable computers, gaming systems, computing tablets, device controllers, or other types of mobile devices. Furthermore, data interface 130 can comprise non-mobile devices possibly including fixed sensors 120A, routers, switches, sensor webs, an appliance, a garment, or other devices capable of capturing data of interest.

Sensors 120A through 120B, cloud 115, and other items within ecosystem 100 can communicate among each other as desired. In more preferred embodiments, elements within ecosystem communicate over one or more wireless protocols, depending on the nature of the element. For example, the major components in the system can utilize high bandwidth protocols possibly including Ultra Wide Band (UWB), Wi-Fi, WiGIG, Multimodal bands, cellular networks (e.g., CDMA, GSM, etc.), or other types of broadband communications. Smaller elements, sensors 120A through 120B for example, can use lower bandwidth protocols including Zigbee, Wi-Fi, wireless USB, Bluetooth, near field communications, or other protocols. The protocols used for exchanging data among elements of ecosystem 100, especially via data interface 130, can be configured to fit the bandwidth needs of the communication channel.

One should appreciate that data interface 130 allows animate or inanimate objects to operate as I/O sources for reasoning engine 160. Animate objects typically include living animals, humans for example, but could also include non-living objects. Preferably animate objects include human beings participating with aspects of environment 110 while other animate living objects can include pets, animals, plants, or other living things. Example non-living animate objects include robots, vehicles, assembly lines, toys, or other items that can move. Inanimate objects are consider to be objects that do not substantially change or move with time including buildings, geological features, books, appliances, or other types of objects. Still further, data interface 130 can be configured to acquire data associated with virtual objects or augmented reality objects. In such cases, data interface 130 can operate as an API capable of providing access to information related to the virtual objects, which allows such virtual objects to operate as I/O interfaces to reasoning engine 160.

Environment data can be obtained according to various modalities including modalities beyond human perception. Human modalities include sensor data representative of the human senses: audible data, visual data, kinesthetic data, olfactory data, or taste data. Non-human modalities comprise a full spectrum of data beyond the human experience and possibly include experimental data, radio frequency data, geologic data, biometric data, medical or genomic data, accelerometer data, magnetometer data, electromagnetic spectrum outside visible light, or other types of data that a human can not perceive directly. Still other types of environment data can also be acquired including search queries, news events, weather data (e.g., barometric data, temperature data, wind data pressure data, etc.), demographics, user identity data, network usage data, or other data that can be captured or measured. The environment data can also include data from different locations, including locations that are geographically separated. For example, network traffic data can be acquired from the National Lambda Rail (see URL www.nlr.net) in the United States while medical data is acquired in India.

As environment data flows into ecosystem 100, the environment data can be processed to generate or otherwise create analyzed aspects of the environment. An analyzed aspect represents an object comprising a processed portion of the environment data that is not necessarily present in the environment per se. For example, a trend in a body temperature or an outdoor temperature can be considered an analyzed aspect of the environment. Analyzed aspects can be bound via object attributes to parts of the environment, possibly bound to data interface 130, a cell phone, a sensor, a user, a patient, a time, a location, or other elements of the environment for example.

Especially preferred analyzed aspects of environment 110 include those representing observed changes in the environment, which can also be converted to a data object that can be analyzed or recognized. Such observed changes, or "deltas", in observed environment metrics have practical applications with respect to medical reasoning engines among other types of reasoning applications. For example, data input into ecosystem 100 can include changes in characteristics of a biometric sensor with respect one or more sensor characteristics. The changes in the characteristics can be indicative of a change in a patient's body possibly including pressure points, airway patency, respiration, blood pressure, perspiration, body fluids, perfusion, or other types of body changes. These changes can be recognized by reasoning engine 160 and influence selection of reasoning rules, which then influences generated hypotheses.

Sensors 120A through 120B can be consider inanimate objects as discussed above, which can be observed by reasoning engine 160. Therefore changes in characteristics of such inanimate objects can be considered aspects of environment 110. Characteristics of such objects can vary depending on how the objects are observed via the output of sensors 120A through 120B. Example characteristics that can be observed from sensors 120A through 120B can include physical characteristics (e.g., size, shape, dimension, mass, weight, material, etc.), electrical characteristics (e.g., resistance, current, voltage, capacitance, reactance, inductance, permeability, permittivity, etc.), mechanical characteristics (e.g., stress, strain, torque, torsion, force, tension, compression, density, hardness, shear, friction, etc.), acoustical characteristics (e.g., spectrum, frequency, wavelength, absorption, amplitude, phase, etc.), chemical characteristics (e.g., reactivity, pH, surface tension, surface energy, etc.), optical characteristics (e.g., absorptivity, color, luminosity, photosensitivity, reflectivity, refractive index, transmittance, spectrum, spectrum, frequency, wavelength, absorption, amplitude, phase, polarization, etc.), or other types of properties. Such properties can be obtained directly from sensors 120A through 120B or indirectly, and reflect changes in aspects of environment 110, a patients body or a building for example.

Environment data can be encapsulated within a data object, possibly in the form of a serialized data structure (e.g., XML, WSDL, SOAP, etc.). Data objects reflect some aspect of an environment as a quantized unit having one or more object attributes describing the data. For example, an image acquired via a mobile phone can be treated as a data object with attributes describing the image (e.g., resolution, data size, color balance, etc.) or metadata (e.g., camera used, photographer identity, time stamps, orientation, location, etc.). In some embodiments, the attributes of the objects are assigned according to a normalized namespace allowing various objects to be easily compared with each other.

Reasoning engine 160 can utilize one or more namespaces when analyzing recognized objects with respect to each other. Some embodiments can store object attributes according to different normalized namespaces where each object can be represented in different fashions. For example, when an object is recognized in an image as a piece of fruit, the object's attributes can be provisioned as a function of two or more normalized namespace. A first namespace might be fruit-specific (e.g., apples, organs, bananas, etc.) where the fruit-specific namespace adheres to a fruit-specific ontology. A second normalized namespace might relate to nutrition and adhere to a nutrition ontology.

One should appreciate that a data object can be more than a file or quanta of data. More preferred data objects can include digital representations of real-world objects or concepts (e.g., people, things, symbols, emotions, etc.) found in a scene in environment 110. Objects can be recognized by features derived from the digital representation (e.g., image, video, audio, sensor data, etc.) captured by sensors 120A or 120B. When an object is recognized or identified, its features (e.g., attributes, properties, characteristics, etc.) can be auto-populated. Suitable techniques for object recognition that can be adapted for use are described in U.S. Pat. Nos. 7,016,532; 7,477,780; 7,680,324; 7,565,008; and 7,564,469. Furthermore, objects can also exist in an augmented reality or even a non-human data space (e.g., networking infrastructure management system, robotic environment (see www.roboearth.org), data analysis engine, etc.). For example, Augmented Reality (AR) object 112 might only exist within data interface 130, but could still be considered a virtual part of environment 110. Thus, recognized objects in environment 110 can include real-world objects, virtual objects, or other types of objects in the data space.

Inference engines (IE) 140 include one or more computing devices suitability configured to apply programmatic reasoning techniques, individually or in aggregate, to the acquired environment data. One main aspect of the inventive subject matter is to discover possible correlations among aspects (e.g., objects, items, concepts, contexts, reasoned facts, etc.) of environment 110 where the correlations can include ones that a person would not ordinarily expect to consider. Inference engines 140 observe the environment data and attempt to establish one or more hypotheses representing a possible relationship or correlation between aspects of the environment. An example expert system that could be suitably adapted for use as an inference engine includes the system described in international patent application WO 88/05574 to Wolf titled "Expert Knowledge System Development Tool", filed Jan. 20, 1987.

Various reasoning techniques can be applied to determine if "reasoned" connections might exist. Logically consistent reasoning techniques can include deductive reasoning, case-based reasoning, or other types of reasoning having consistent boundaries. More preferred reasoning techniques allow inference engines 140 to make a leap beyond conclusions that have stringent necessary and sufficient conditions to conclusions that could lack sound premises; thus creating the opportunity for discovery or sparking creativity. Additional reasoning techniques allowing for such a leap include abductive reasoning, indicative reasoning, fuzzy logic, or other types of reasoning that lack a requirement for necessary or even sufficient criteria. One should appreciate that a hybrid; for example applying deductive reasoning to premises generated from abductive reasoning to form interesting hypothesis. UK patent application publication GB 2 278 467 to Imlah titled "A knowledge based system implementing abductive reasoning", filed May 20, 1993, describes applications of abductive reasoning techniques that can be suitably adapted for use with inventive subject matter.

Examples for different styles of reasoning can also include forward chaining or backward chaining reasoning as disclosed in European patent application publication 0 453 874 to Highland et al. titled "A computer based inference engine device and method thereof for integrating backward chaining and forward chaining reasoning", filed Apr. 10, 1991. Another example, includes U.S. Pat. No. 7,418,434 to Barry titled "Forward-Chaining Inferencing", filed May 13, 2005. The disclosed techniques could be suitably adapted for use with the inventive subject matter. Examples of case-based reasoning are discussed in U.S. Pat. No. 5,581,664 to Allen et al. titled "Case-based Reasoning System", filed May 23, 1994.

Another technique capable of generating hypotheses includes metaphorical mapping. Metaphorical mapping comprises establishing similarities between known concepts and a current concept under evaluation. A known concept can be represented by relationships among known objects (e.g., data object, sensed objects, recognized objects, recognized concepts, etc.) where each of the objects or relationships can be characterized by attributes, possibly arranged according to one or more concept maps. U.S. patent application 2010/0287478 to Avasarala et al. titled "Semi-Automated and Inter-active System and Method for Analyzing Patent Landscapes", filed May 11, 2009, describes techniques for building and comparing concept maps in a patent landscape. Such techniques can be readily adapted for use herein where concept maps are built according to recognized aspects in environment 110. Inference engine 140 can use one or more of the previously discussed reasoning technique to generate a possible similarity between the features of a current concept to the features of known concepts or ontologies. If inference engine 140 determines a sufficient similarity exists via a satisfaction criteria, then the known concept can be considered a metaphor for the current concept. Each known concept map can be considered a manageable object and can comprise extrapolation paths representing a algorithmic structure through which a metaphor can be extended. A hypothesis can then be drawn by extending the current concept along extrapolation paths according to the known context. One example of generating hypotheses that could be suitably adapted for use includes those described in U.S. published patent application 2011/0231356 to Vaidyanathan et al. titled "Flexscape: Data Driven Hypothesis Testing and Generation Systems", filed Jul. 1, 2010.

With respect to metaphorical mapping, consider an example scenario where reasoning engine 160 identifies a round red object, perhaps a playground ball. Inference engine 140 generates a concept map associated with the ball. Based on the structure of the ball's concept map, inference engine 140 might identify that an apple concept map might be a reasonable metaphor for the ball. The apple concept map can include extrapolation paths that could include concepts relating to growing, harvesting, eating, nutrition, varieties, or other concepts related to apples. These extrapolation paths can then be applied to the ball concept and might yield a hypothesis that balls can be harvested, or have different varieties. Although the hypotheses might seem nonsensical at first review, they can spark additional cognitive reasoning or conclusions that can have value for creativity, imaginative, or emotional purposes. For example, harvesting balls might metaphorically map to picking up balls after a recess in a school.

Inference engines 140 can also take on many different forms. Examples include dedicated computing devices; a server or search engine for example. Inference engines 140 can also be deployed within data interface 130, a mobile phone for example, when quick localized reasoning would be beneficial. Yet further examples including networking nodes operating as inference engines 140 and also operate as a general data transport. For example, inference engines can be deployed within a switch, a router, a web server, a gateway, an access point, a firewall, or other type of network device. For example, the nodes of the National Lamba Rail can function as an inference engine operating on medical or genomic data flowing through the network where the medical data can be considered a non-human modality associated with a medical data space.

It is specifically contemplated that inference engine 140 can comprise a member of a distributed reasoning engines 160 as illustrated where various elements exchange hypotheses among each other. In such an embodiment, the environment data collected by inference engines 140 can also include previously generated hypotheses. Thus, reasoning engines 160 are able to build on and learn from previous experiences or previously reasoned facts; even reasoned facts that are not necessarily true. One should appreciate that such reflexive reasoning allows the reasoning engine to observe itself, creating a reasoning engine reflexive data space. One aspect of the inventive subject matter is considered to include management of such reflexive reasoning to ensure the behavior converges or diverges appropriately. Reflexive management can include tracking number of iterations through a reasoning loop, number of nested hypotheses, uncertainty score or merit scores of hypotheses, or other metrics. Should the metrics satisfy a reflexive observation criteria, the reflexive reasoning can be halted appropriately. Uncertainty in a reasoning sequence can be based on techniques disclosed in U.S. Pat. No. 4,860,213 to Bonissone titled "Reasoning System for Reasoning with Uncertainty", filed Oct. 1, 1987. Bonissone describes propagating uncertainty information through a reasoning based system. Such an approach can be further adapted for assigning merit scores or rankings to hypotheses.

An astute reader will appreciate that a formulated hypothesis does not necessarily equate to a true hypothesis in view of the reasoning techniques. To establish validity, at least at some level, of a hypothesis, a reasoning engine can further comprise one or more validation modules (VM) 150. Validation module 150 can be configured to run one or more experiments on the data space (i.e., environment 110) in an attempt to validate the hypothesis through controlling acquisition of the environment data. For example, inference engine 140 might hypothesize that a person is always at a specific location at a time of day based on the person's cell phone location. Then validation module 150 can then instruct the cell phone (e.g., data interface 120) to acquire location data, possibly GPS data, at the specified time. If the acquired data matches the hypothesis, the hypothesis is likely valid, or a merit score of the hypothesis can be adjusted appropriately.

Validity of a hypothesis can be determined with respect to one or more criteria sets, possibly according to differing dimensions of relevance. In the previous example, validity was determined by empirical data. Rather than experimentally obtaining validation data, the validation module could also seek validity through subjective data by constructing a survey targeting a demographic. Such an approach is considered advantageous when determining when a demographic might be interested in a hypothesis representing an imaginative construct, a creative work, or even an emotion.

One should appreciate the difference between seeking feedback from a user versus empirical evidence from the data space to validate a hypothesis. Seeking feedback might include submitting a question back to a user where the user validates the hypothesis. Empirical evidence includes controlling acquisition of the environment data according to a validation plan. The validation plan could include instructions from one or more of the validation modules 150 to generate commands, which are submitted to data interface 130. The submitted commands can control acquisition of data from sensors 120A through 120B. Further, validation modules 150 can inject data back into environment 110 according to the validation plan to observe changes in the environment 110.

Hypotheses are considered dynamic objects and in some cases can change with time. Inference engine 140 can continually generate hypotheses based on information flow from sensors 120A through 120B or other information relating to environment 110. Some hypotheses can be generated in real-time based on the ever changing nature of environment 110, while other hypotheses might be generated over extended periods of time once a suitable number of observations have been acquired. For example, reasoning engine 160 and its components can store a hypothesis object in their corresponding memories. As additional data is made available, the hypothesis object can be modified in real-time; at the speed of memory accesses (e.g., Flash, RAM, hard disk, solid state disk, etc.). Thus, a user can observe changes to a hypothesis as it evolves over time.

In some scenarios a hypothesis has a temporal nature where the hypothesis's suspected correlation has time-based values. For example, a hypothesis might indicate a person's preference for apples. However, the validity of the hypothesis might vary throughout a day, week, month, or year. A hypothesis merit score or validity score can change with time as new data becomes available.

One of the aspects of the inventive subject matter is considered to include establishing validity according to one or more dimensions of relevance. Consider a case where inference engine 140 generates a hypothesis that a segment of the population would be interested in a topic; a movie or game for example. Validation module 150 can recognize there are many dimensions of relevance with respect to the population possibly including age or gender, which represent just two dimensions of relevance. To validate the concept, validation modules 150 can create a survey and present the survey only to individuals according to age or gender, or other dimensions of relevance. Validation module 150 might discern, or otherwise learn, that the hypothesis is valid for one gender but not another. Such an approach can be extended to many types of hypotheses. All dimensions of relevance are contemplated.

Although the above discussion is presented generically, there are many arenas where such reasoning engines can be used. As inference engine 140 operates to generate or validate hypotheses, they effectively learn about external environments 110. One major distinction relative to previous AI techniques is the disclosed reasoning engines can directly, or indirectly, interact with the environments 110 to learn if the hypotheses are valid or in valid. Furthermore, reasoning engines 160 can operate regardless of the type of environment being evaluated. Example environments can include a global environment, a real-world environment, a virtual environment (e.g., within a game world), an augmented reality mixing real-world and virtual world objects, a data space environment (e.g., non-human space), or other types of environments 110. An example data space environment could include network infrastructure management where network management data is exchanged among networking nodes. Reasoning engine 160 can operate as a network management functionality deployed within one of the nodes.

A hypothesis is considered to represent more than a static correlation between or among data points. A hypothesis can also represent human experiences as briefly referenced above. For example a hypothesis can represent an intuition, an imaginative construct, a creative work, an emotion, or other type of traditional human experience. Consider intuition for example. A reasoning engine 160 can include multiple layers of inference engines where a sub-engine generates a hypothesis, and might even validate the hypothesis to some degrees. The sub-engine sends the hypothesis up to a next layer as an object where the next layer uses the hypothesis as input for its evaluations. Thus, the sub-engine's hypothesis can be considered intuition percolating up through the reasoning engine. Another suitable technique that can be adapted for use for establishing intuition includes those described by U.S. Pat. No. 5,175,795 to Tsuda et al. titled "Hybridized Frame Inference and Fuzzy Reasoning System and Methods", filed Jul. 13, 1989. Emotional hypothesis could be as simple as differentiating between aspects of the environment (e.g., sounds, sights, facial expressions, objects, etc.) and generating a hypothesis relating reactions of individuals relative to observed aspects of the environment (see FIG. 3). One can consider reasoning engine 160 to be emotionally aware of an environment based on the type or tenor of the captured data (e.g., music, art, nature, tone, etc.) mapped to appropriate emotional concept maps.

In view that reasoning engine 160 can also interact with an environment, reasoning engine 160 can also inject data back into the environment based on the hypothesis, preferably according to a validation plan. The injected data can be presented through one or more presentation modules. In some embodiments, the injected data can represents surveys as discussed above, advertisements, recommendations, commands, or other types of data that affect the environment.

Although the above discussion is presented in broad brush strokes, there are many practical applications. Example applications including advertising, network management, experimental research, content creation, innovation, or other areas where humans excel over machines. Still, it is expected that human interaction would be advantageous to select validated hypotheses for actual application.

One interesting application can include providing individuals with a personalized reasoning engine or inference engine where the personalized inference engine operates according to dictated or learned preferences of the individual. The personalized inference engine can retain access to other inference engines if desired to gain from other experiences. In some embodiments, the personalized inference engine can operate as a reasoning companion that observes ambient data, possibly in real-time, surrounding an individual. The companion can reason that the individual might be interested in a topic (i.e., a hypothesis) based on the ambient data (e.g., idle conversations, images, etc.). To validate the hypothesis, the companion can present the topic to the individual, possibly in a non-obtrusive manner, or alter the environment and observe the individual's reaction. Through learning more about the individual by validating hypotheses, the reasoning companion becomes a stronger companion capable of anticipating the individual's needs or desires based on a context derived from ambient data.

Figure 2:
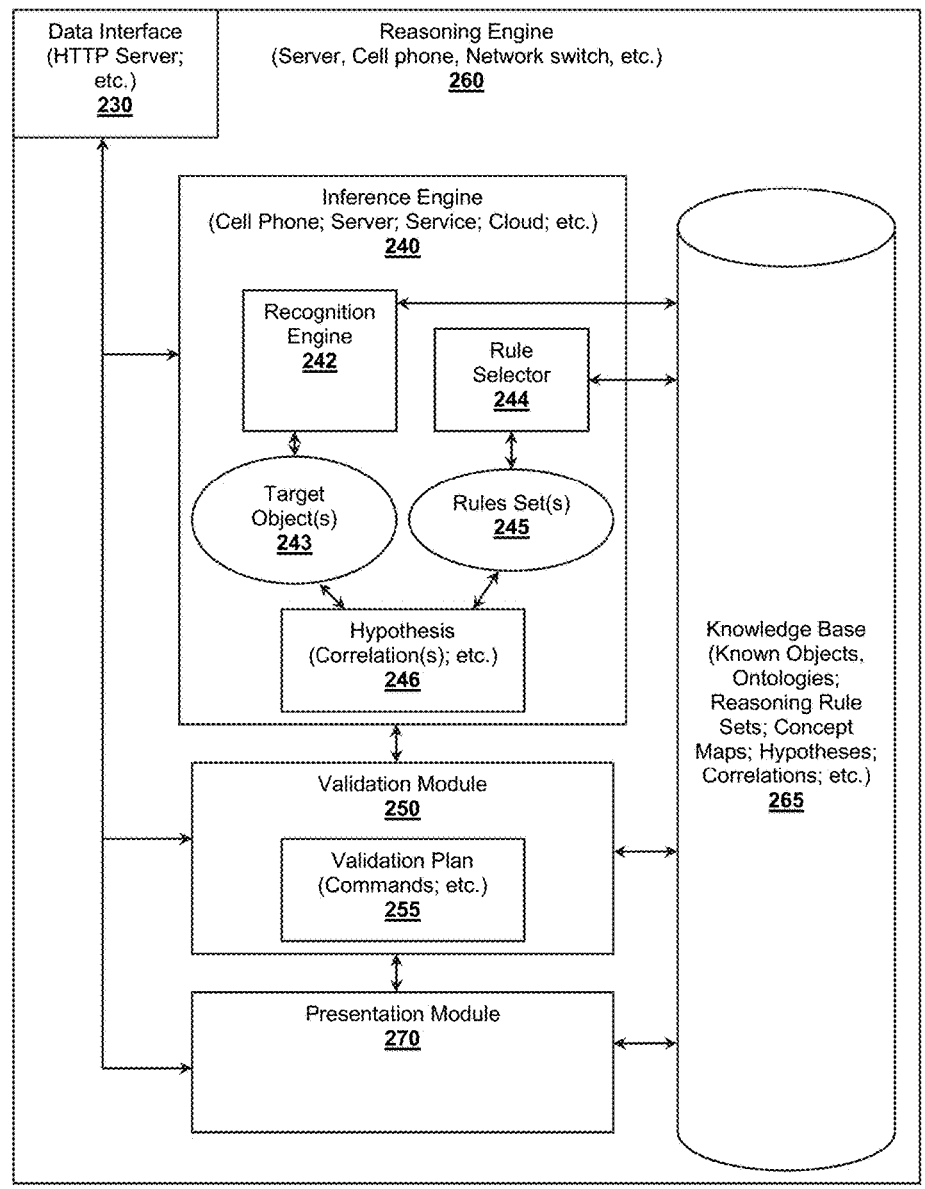
FIG. 2 is a schematic of a reasoning engine.

FIG. 2 presents a more detail view of a possible reasoning engine 260. Reasoning engine 260 can be implemented according to various techniques. In some embodiments, reasoning engine 260 operates as an Internet based service, possibly a for-fee service, in a similar fashion as a search engine. For example, reasoning engine 260 could provide reasoning services to users for free. As inquiries are submitted to reasoning engine 260, the reasoning engine can present advertisements along with hypothesized conclusions. Advertisers can pay for advertisements based on reasoning techniques used for a topic. For the purposes of discussion, reasoning engine 260 is presented as a server platform. However, one should appreciate that reasoning engine 260 can also be deployed within a mobile device, a network switch, a car navigation system, or other computer-based device. It is especially contemplated that reasoning engine 160, or portions of reasoning engine 160, can be distributed across multiple computing devices from an end user device (e.g., a cell phone) through networking infrastructure (e.g., switches, routers, ISPs, etc.), to cloud-based services (e.g., virtual servers, Amazon® EC2, etc.) where each portion communicates reasoning information or objects using appropriate protocols (e.g., WSDL, SOAP, HTTP, TCP/IP, etc.).

With respect to network switches, example switches that could host reasoning engine 260 could include those offered by Cisco® (e.g., Cisco Catalyst, Nexus, etc.) or Juniper® (e.g., EX4200, EX4500, etc.). It is considered advantageous to deploy reasoning engine 260 within such infrastructure because the networking infrastructure itself can function as a computational fabric as acquired environment data flows from node to node. Switches capable of operating as a computational fabric that could operate as reasoning engine 260 are discussed in U.S. Pat. Nos. 7,904,602; 7,548,556; 7,603,428; U.S. published application 2010/0312913; and U.S. applications having Ser. Nos. 13/024,176 and 13/024,240.

Reasoning engine 260 can include one or more of data interface 230. In the example shown, data interface 230 comprises an HTTP server through which remote devices interact with reasoning engine 260. Preferably data interface 230 is configured to acquire or receive sensor data or digital representations of a scene having one or more objects. For example, data interface 230 could couple with a cell phone over the Internet or cell network. Alternatively, data interface 230 could couple with other information sources including weather stations, news or media outlets, stock markets, web sites or services, radio stations, or other sources of data.

Reasoning engine 260 preferably includes one or more of knowledge base 265. Knowledge base 265 represents one or more databases storing information related to reasoning processes. In some embodiments, the knowledge stored in knowledge base 265 is personalized to a specific individual. In such embodiments, a person's reasoning engine 260 might function differently than another person's reasoning engine 260 even when the same reasoning rules are applied. In other embodiments, knowledge base 265 can include information across a population or demographic, or other across type of classifications (e.g., geographic, retailers, affiliations, etc.).

Knowledge base 265 can store a broad spectrum of objects in support of reasoning engine 260. Example objects include known target objects that reasoning engine 260 can recognize, ontologies describing domain-specific information, reasoning rule sets, previously generated hypotheses, reasoned knowledge or facts, suspected or established correlations, or other information. It should be appreciated that each of these types of objects can be managed as distinct objects where each type of object comprises attributes describing the nature of the object. As discussed previously the object attributes can adhere to one or more normalized or common namespaces, which not only allows for comparison of one object to another in the same domain, but comparison of one object to other types of objects even when the objects are across knowledge-specific domains. For example, a hypothesis generated with respect to mapping an unknown word of a language to a recognized target object (e.g., an apple) could be compared to correlations derived from analysis of patents even though the two concepts are widely different.

Preferably reasoning engine 260 comprises one or more of inference engine 240. Inference engine 240 represents the component of the ecosystem configured to derive interesting relationships among recognized objects associated with an inquiry. Inference engine 240 as illustrated is configured to receive an inquiry relating to one or more aspects (e.g., symbols, objects, utterances, observations, etc.) of an environment. In some embodiments, the inquiry could be obtained directly via data inference 230 in the form of a digital representation of the environment or the aspects. It is also contemplated that the inquiry can be obtained via other avenues as well. For example, the inquiry could be submitted through a search engine, Application Program Interface (API), or even internally generated.

As the environment data associated with the aspects of the environment enters inference engine 240, it can be passed to recognition engine 242. Through recognition engine 242, inference engine 240 is configured to recognize the aspects of the environment as target objects 243, where each of the target objects 243 has object attributes as discussed previously. Although target objects 243 can represent items identified directly from the environment data, one should further appreciate that target objects 243 can include generated target objects internal to inference engine 240: previously generated hypotheses or reasoned facts, suggested correlations, validation plans, or other objects.

Recognition engine 242 can recognize the aspects of the environment as the target objects 243 through various techniques, or even combined techniques. In some embodiments, recognition engine 242 analyzes the environment data to derived one or more data features where the data features represents characteristics of the data itself in addition to the features of the data content (e.g., objects, sounds, symbols, etc.) associated with items in the scene. Example imaged-based data features could include those derived from Scale Invariant Feature Transform (SIFT; U.S. Pat. No. 6,711,293), Virtual Simultaneous Localization and Mapping (vSLAM™; "The vSLAM Algorithm for Robust Localization and Mapping", Karlsson et al., Proc. of Int. Conf. on Robotics and Automation (ICRA) 2005), Speeded Up Robust Feature (SURF), Visual Pattern Recognition (ViPR), or other data features. The values generated from such features can be used as an index into a knowledge base to retrieve known target objects 243 having similar features. Thus, recognition engine 242 can recognize aspects of the environment as target objects 243. Other types of data features beyond visual modality can also be used using known techniques for each type of modality.

One should appreciate that recognition engine 252 can also operate in reverse. When aspects of the environment do not map to known target objects 243, then recognition engine 242 can instantiate a target object 243 as a newly discovered object in the knowledge base where the object attributes are provisioned from the information available from the environment data. For example, a user might wish to discover relationships associated with an apple. The user images an apple, which is not known for the sake of argument. Recognition engine 242 identifies that there is an unknown object in the environment data. Inference engine 240 supplies additional information associated with the unknown object (e.g., color, size, position, orientation, location, etc.), which is then used to provision the attributes of the object. The object can then be stored in the knowledge base. Based on additional information, inference engine 240 might at a later date bind more meaningful data to the object (see FIG. 3); that the unknown object is a fruit called an apple.

Inference engine 240 can also include one or more of rule selector 244. Rule selector 244 configures inference engine 240 to select one or more of reasoning rules set 245 from knowledge base 265 as a function of the environment data and object attributes of the recognized target objects 243. Rule selector 244 can select desired reasoning rules sets 245 via one or more selection criteria. In some embodiments, rule selector 244 maps target object attributes to known concept maps, which can include pointers to preferred types of reasoning: deductive, abductive, inductive, ampliative reasoning, case-based reasoning, metaphorical mapping, forward chaining, backward chaining, analogical reasoning, cause-and-effect reasoning, defeasible or indefeasible reasoning, comparative reasoning, conditional reasoning, decompositional reasoning, exemplar reasoning, modal logic, set-base reasoning, systemic reasoning, syllogistic reasoning, probabilistic reasoning, paraconsistent reasoning, or other types of reasoning.

One should appreciate the rule selector 244 could vary across a broad spectrum of capabilities from one inference engine 240 to another based on the configuration of inference engine 240. In embodiments where reasoning engine 260 as been adapted for personal use, rule selector 244 can be configured to weight selection of a non-logical reasoning over logical reasoning because the user wishes to discover relationships that might be relevant to a work of art or creativity. While another person's reasoning engine 240 might weight selection of cause-and-effect reasoning (e.g., cause-to-effect reasoning, effects-to-cause reasoning, the Bradford Hill Criteria, etc.) because more rigorous reasoning is required, possibly for use in medical diagnosis or scientific research. Thus, hypotheses 246 generated from the selected reasoning rules set 245 could vary widely even if target objects 243 are the same from one user to another.

Inference engine 240 is preferably configured to establish one or more of hypothesis 246 according to the one or more selected reasoning rules set 245. Hypothesis 246 represents a suspected correlation that might exist among target objects 243. As discussed previously, the suspected correlation does not necessarily have to be valid or even true. Rather hypothesis 246 seeks to fulfill the goal of an incoming inquiry, which is to seek a possible relationship based on recognized aspects of the environment. Hypothesis 246 can be presented via one or more of presentation module 270 back to the inquirer.

In some embodiments, inference engine 240 comprises at least one of validation module 250 coupled with inference engine 240. Validation module 250 is preferably configured to construct one or more of validation plan 255, which outlines a path to establish validity of hypothesis 246. Validation plan 255 can be derived from the suspected correlation embodied by hypothesis 246. Information from the suspected correlation can include types of environment data that can be used to further corroborate the correlation. Based on validation plan 255, validation module 250 can be configured to request updated environment data with respect to the aspects of the environment via data interface 230. Validation plan 255 can include a direct query to a user to seek validation. However, a more preferred approach includes validation module 250 controlling acquisition of the environment data according to validation plan 255 without user involvement. In some embodiments, validation module 250 submits sensor commands to data interface 230, which in turn controls how, when, which, where, what or other aspect of sensor data collection. In a very real sense, validation module 250 conducts an experiment on the target data space to see if the suspected correlation holds. Thus, validation module 250 can inject data back into the environment via presentation module 270 and data interface 230.

Validation module 250 is further configured to generate a derived relationship among the aspects of the environment as a function of the validation plan 255 and the updated environment data. The derived relationships do not necessarily have to be a binary true or false, but can include a spectrum of values. As statistics are built up over time, the derived relationships cause an increase or decrease a merit score associated with hypothesis 246.

Figure 3:
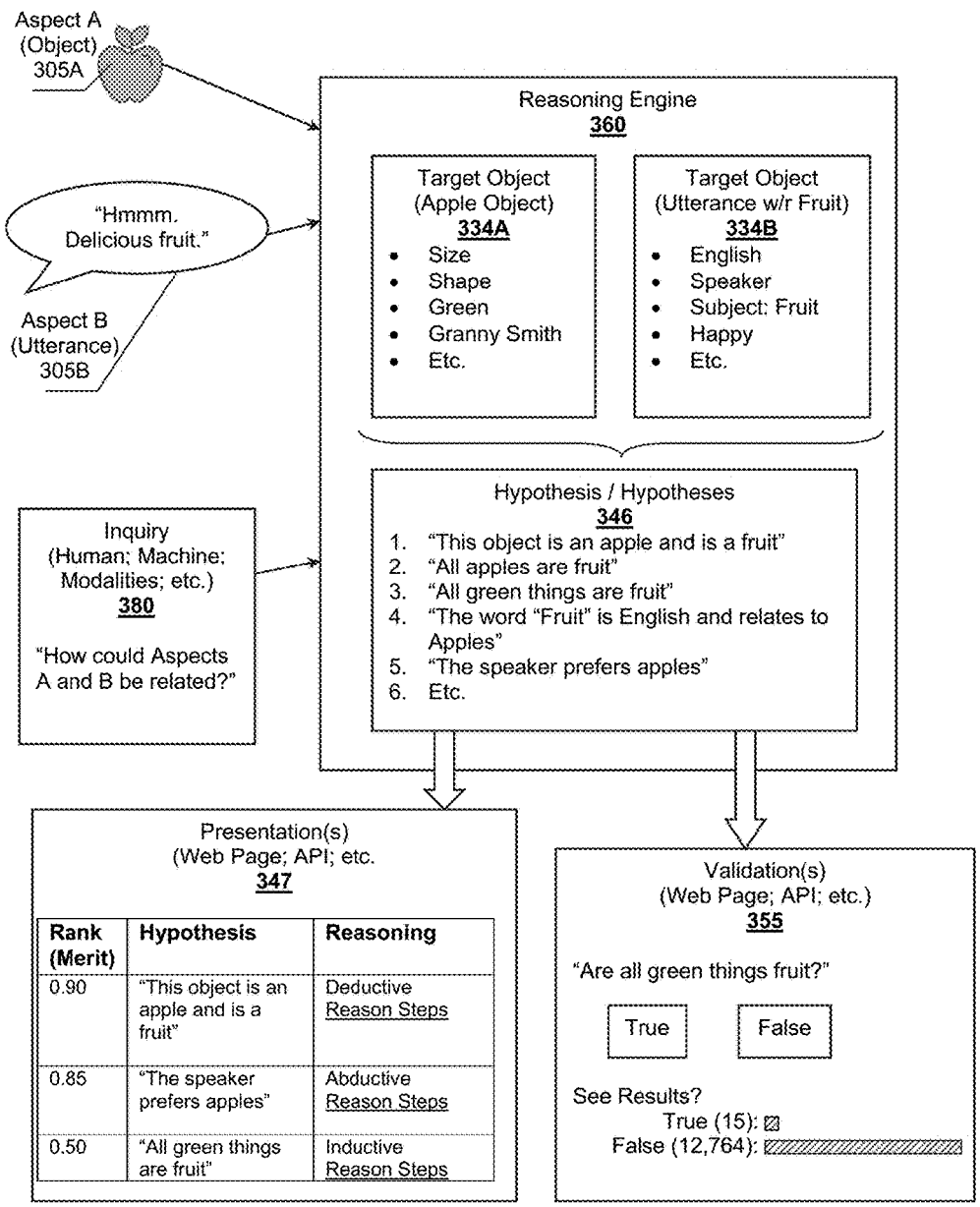
FIG. 3 is a schematic of data flow through a reasoning engine.

FIG. 3 illustrates a more specific example where reasoning engine 360 is utilized as a form of Rosetta stone where reasoning engine 360 collects information associated with an object, an apple in this case, according to different languages, English in this case. Although the following discussion references the English language, one should appreciate that the techniques are language independent. Therefore, reasoning engine 360 can infer conceptual information associated with a recognized object in a language independent fashion.

In the example shown, reasoning engine 360 receives environment data related to environmental aspect 305A and aspect 305B. Aspect 305A represents imaged data (e.g., visual modality) related to an apple and aspect 305B represent audio data (e.g., auditory modality) for an utterance. The environment data can be processed or pre-processed by the acquiring device (e.g., cell phone, sensor, etc.), an intermediary device (e.g., search engine, etc), or reasoning engine 360 as desired. Reasoning engine 360 receives the environment data associated with aspects 305A and 305B and attempts to recognize the aspects as target objects. The environment data can be collected with intent, where a user submits the information, possibly via inquiry 380, or without intent. For example, reasoning engine 360 can be configured to collect ambient data as data flows through a sensor, gateway, network switch, cell phone, or search engine where ambient data triggers formation of inquiry 380.

Reasoning engine 360 recognizes aspects 305A and 305B as target object 334A and 334B respectively. Target object 334A is recognized as having a set of object attributes including size, shape, color, name, or other information related to aspects 305A. Further, target object 334B is recognized as an utterance relating to fruit. In the example shown, reasoning engine 360 is able to establish that target objects 334A and 334B are subject to inquiry 380 through various techniques. In one scenario, inquiry 380 specifically references aspects 305A and 305B. In other scenarios, aspects 305A and 305B might be related to because of relative proximity to each other in location, in time, with respect to the user, or other attribute.

Inquiry 380 can take on many different forms. As discussed previously, inquiry 380 can be an explicit inquiry submitted by a user or could be an auto generated inquiry generated by reasoning engine 360 or other device. In some embodiments, inquiry 380 can be auto generated as part of a validation plan. Thus, inquiry 380 can comprise human understandable modalities, machine understandable modalities, or other types of modalities. In the example shown, inquiry 380 as translated is submitted to reasoning engine as "How could aspects A and B be related?", which causes reasoning engine 360 to begin an analysis.

The term "inquiry" is differentiated from the term "query" within the context of this document. A query is considered to be a request for existing information that relates to the queried subject matter. A query is keyword-based where a search engine or other type of database returns a result set of existing documents or information that match keywords in the query. An inquiry is considered to be a request for augmenting knowledge, resolving doubt, or solving a problem rather than mere a set of keywords. With respect to the example shown, inquiry 380 is an inquiry because the request relates to possible relationships that may or may not exist, or have not yet even been considered previously. Inquiry 380 is not considered a query because the request does not necessarily relate to a keyword-base search for existing documents.

Reasoning engine 360 accepts inquiry 380 and selects one or more reasoning rules sets, in this case multiple rule sets are selected for use to establish hypotheses 346 to explore the possible relationships among target objects 334A and 334B. Hypotheses 346 represents a set of possible inferences generated by reasoning engine 360 for the specific situation where the hypotheses 346 are ranked according to some criteria as discussed with respect to presentations 347. Hypotheses 346, again, do not necessarily have to be true or valid. Rather, hypotheses 346 represent an exploration of the conceptual space or spaces associated with target objects 334A and 334B.

For the current example, reasoning engine 340 hypothesizes that the English word "Fruit" applies to an apple object. Assuming that validity of such a hypothesis survives validation, to within a validation criteria, reasoning engine 340 can update attributes of target object 334A to reflect that target object 334A is a "Fruit" as least in English. Thus the reasoning engine 360 can continually infer relationships among words in any language and target object 334A and can auto populate target object 334A with language-specific meaning. Recall that target objects 334A and 334B can have attributes that adhere to different ontologies or namespaces. Therefore, reasoning engine 360 can map the language-specific information to a proper namespace based on the language used or the concepts derived from the environment data. Through such a mapping reasoning engine 360 can operate as a Rosetta stone among languages built on inferences generated from recognized objects or concepts.

Hypotheses 346 are presented as presentations 347, which could be rendered within a browser on a user's computing device as illustrated. However, presentations 347 could also be feedback into reasoning engine 360 as new objects for further analysis or convergence on additional hypotheses. In the example shown, presentations 347 renders hypotheses 346 in a ranked manner according to a merit score.

The merit scores can be a single valued measure of validity for each hypothesis as illustrated. The validity merit score can be derived based on the type of reasoning used to generate the hypothesis. For example, a hypothesis reasoned according to deductive reasoning (see hypothesis 1 of hypotheses 346) likely has a higher validity than a hypothesis reasoned through inductive reasoning (see hypothesis 3 of hypotheses 346). As reasoning engine 360 develops confidence that a hypothesis is valid, the merit score can change appropriately. In such scenarios, the rankings in presentations 347 can change with time.

The merit scores presented in presentations 347 are illustrated as single valued scores, or as having a single dimension of relevance. One should appreciate that merit scores can be multi-valued where each value represents a different dimension of relevance. For example, validity might have value for medical diagnosis, but lacks relevance with respect to an imaginative, creative, or emotional inference. Thus, each hypothesis could include numerous merit scores that are valued as a function of how the various reasoning rules sets map to each type of inference.

In view that hypotheses 346 are not necessarily true or valid based on the type of inference that is desired to be used, reasoning engine 360 can seek one or more of validations 355. In the example shown, validations 355 are generated by a validation module and are directed to seek explicit validation from a user for a hypothesis. In this case, the validation module determines that "All green things are fruits" is not a valid hypothesis. Although reasoning engine 360 can employ explicit validation, reasoning engine 360 can also seek indirect or empirical validation through conducting an experiment. For example, the validation module can be configured to submit a validation request to another user, possibly in a different language. The submitted request could be of the form "Would you like a piece of fruit, an apple perhaps?". Note the request does not seek explicit validation, rather reasoning engine 360 uses its inferred hypothesis as practical knowledge to see if the hypothesis holds based on how an entity in the data space reacts.

Presentations 347 include additional information beyond hypotheses 346 and their associated merit scores. Preferably, reasoning engine 360 also presents how hypotheses 346 were reasoned, including the reasoning steps taken. Such an approach is considered advantageous because the user (e.g., person, machine, etc.) can obtain a better understanding of the "creative" process behind the assertion, which can trigger additional creative thoughts in the user.

Figure 4:
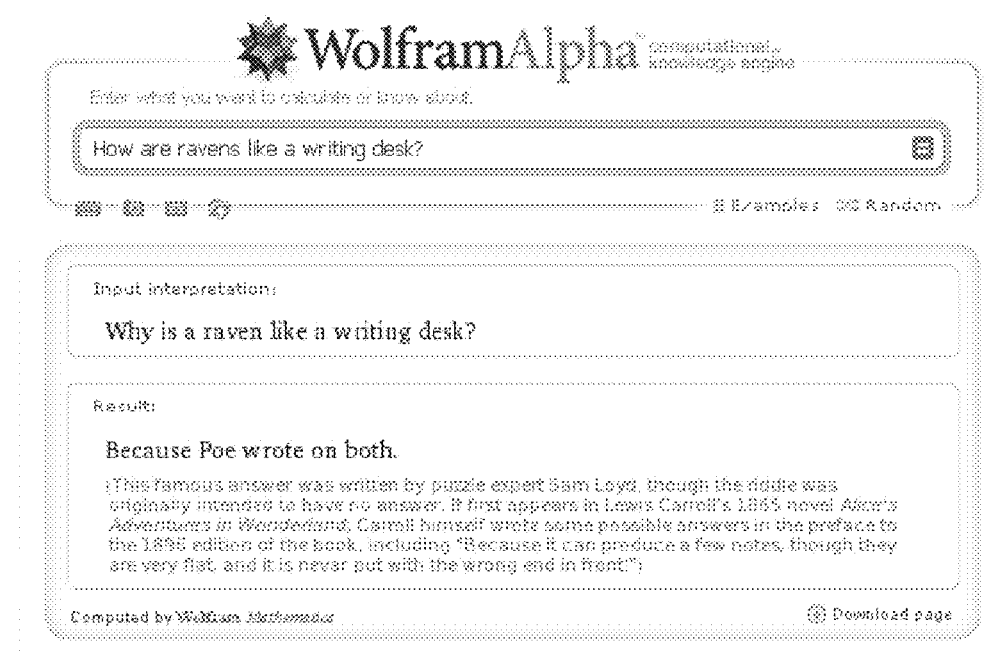

Consider a real-world situation. The question "How are ravens like a writing desk?" was submitted to WolframAlpha.com (see FIG. 4). Such a question is nonsensical and was intended to be so. WolframAlpha™ returns a query-based response "Because Poe wrote on both" based on retrieval of documents, but does not return inferred reasoning on how a raven could indeed be like a writing desk. In the disclosed approach, the user would be presented with one or more hypotheses along with reasoning behind the hypothesis. It is also contemplated that a hypothesis of NULL could be generated by the disclosed approach (i.e., "there does not appear to be a reason why ravens are like a writing desk"). The disclosed approach allows for expanding the reasoning, creativity, imagination, or even emotional awareness of the user especially in view that the hypothesis can be considered creative works, imaginative constructs, or even emotions.

The inventive subject matter can be applied across a wide variety of markets including commercial markets, educational markets, entertainment markets, medical markets, or other types of markets. Consider medical reasoning for example. A reasoning engine as disclosed can be configured to operate within a medical data space. For example, a medical reasoning engine can observe how healthcare providers (e.g., doctors, surgeons, pharmacists, etc.) treat patients and observe results obtained from the treatment protocols applied to the patients. In such a scenario, the reasoning engine can view the treatment protocols and results as aspects of the medical data space environment. Further, reasoning engine can generate one or more hypotheses relating to the positive, or negative, outcome from the treatment protocols. In such embodiments, it is unlikely that the reasoning engine will alter the behavior of the treatment protocol. However, the reasoning engine can offer the hypotheses as recommendations on changes to the treatment protocol.

The medical hypotheses can be validated, to some extent, by the reasoning engine through the reasoning engine seeking additional data across the medical data space according to a validation plan. For example, the medical reasoning engine might hypothesize that a group of patients belonging to a specific demographic appears to respond to a specific treatment protocol or surgery. The reasoning engine can then capture sensor data from other patients within similar demographics, or even dissimilar demographics, in a non-intrusive fashion and then use the sensor data to determine if the hypothesis is supported or not supported. Based on the validation process, the reasoning engine can alter its recommendations. Such techniques can be applied to surgeries, prescriptions, chemotherapy, blood work analysis, family history review, or other types of medical related activities.

The disclosed reasoning engines can also be applied to commercial reasoning. Commercial reasoning engine have applicability to both sellers and buyers. From the seller's perspective, a vendor or other type of retailer can leverage the services of a reasoning engine in an attempt to figure out how or why revenues change with time. The vendor can supply vendor information into the reasoning engine from various sources. The vendor information could include sales figures, promotions, employees, coupons, planograms, customer demographics, or other information. The vendor's reasoning engine can then offer hypotheses about how aspects of the business directly or indirectly relate to business performance metrics. The vendor's reasoning engine can further offer recommendations (i.e., a validation plan) on altering the business to confirm or invalidate the hypotheses. From a buyer's perspective, a buyer can also utilize a personal reasoning engine configure to observe the buyer's behaviors and hypothesize about the buyer's preferences. As the reasoning engine evolves and learns about the buyer, the reasoning engine can generate recommendations as part of a validation plan based on the hypothesized preferences. As data from a goods and services data space flows into the buyer's reasoning engine, the engine can infer that the buyer might be interested in newly presented promotions (e.g., advertised goods and services, coupons, deals, sales, etc.). The buyer can then be enabled to purchase the products (e.g., movie tickets, music, videos, games, products, etc.) according to the promotions. In some embodiments, hypotheses are validated through auto construction of a promotion according to the validation plan. More specifically, a promotion or coupon could correspond to a validation activity. Regardless of the vendor's or buyer's perspective, the reasoning engine can conduct its inference analysis based on the attributes of the entities involved (e.g., buyer, seller, consumers, etc.) as well as product features.

Another interesting application of the disclosed techniques includes applying reasoning engines for educational purposes. Students can leverage reasoning engines in different manners depending on the lessons to be learned. In some embodiments, the reasoning engines can illustrate to a student how to assess incoming information and derive meaningful knowledge from the information. For example, when working in math or science, the reasoning engine can show the student how deductive reasoning is applied and how it can provide necessary and sufficient conditions for a true result: If A=B and B=C, then A=C for example. Alternatively, educational reasoning engines can be configured to generate hypotheses lacking sufficient conditions for validity as a challenge to the student to determine the validity of the hypothesis. Still further, educational reasoning engines can be configured to reason in a manner that is age-appropriate for the student, or appropriate for the student's capabilities. A young student might only be able to process simple reasoning rules (e.g., deductive reasoning) while an older student might be able to process more complex reasoning rules (e.g., abductive, hybrid reasoning techniques, forward-chaining, etc.). The student's reasoning engine can then evolve with the student.

As discussed previously reasoning engines can be applied to translation. A translation reasoning engine can generate hypotheses that represent a suspected correlation that a word in a language, or languages, corresponds to one or more conceptual objects. As a Rosetta stone style translation reasoning engine continues operate based on information obtained, its capabilities in translating concepts from one language to another improve. Further, translation reasoning engines can provide users with hypotheses indicating possible translations obtained from foreign languages. For example, a user might travel from the United States to China. As the user interacts with one or more Chinese persons, the English speaker can use their cell phone operating as a translation reasoning engine to present hypotheses representing the conceptual meaning being discussed in Chinese. Such hypotheses can take the form of translated information related to a concept and presented on the cell phone in both English and Chinese, and can be further ranked according to merit score indicating a likelihood of a match between the English and Chinese conceptual translations. This approach allows both the English language speaker and Chinese speaker to identify their actual meaning.

Still another type of reasoning engine can include game-based reasoning engines, which can be incorporated into computer games. The reasoning engines can observe one or more players in a game to generate hypotheses about how a player or players play the game as individuals or in groups. As the reasoning engine develops hypotheses, the reasoning engine's validation module can alter the game behavior to seek validation of the players' behaviors. If validated, or even invalidated, the reasoning engine can then cause the game to alter its AI behaviors to increase or decrease the difficulty of the game. Thus, the reasoning engine can conduct automated experimentation on one or more game players to increase the play value of the game. In view that the reasoning engine is able to monitor more than one data source, the reasoning engine can observe the players' real-world reactions to the game and determine their emotional response to the changes, which can be mapped to a "fun" value for the players.

Yet another example of practical application of reasoning engines includes robotic reasoning engines. Reasoning engines can be deployed in various house hold or commercial robots allowing the robots to reason and learn how best to operate in their environments. Consider the iRobot® Roomba®, a popular consumer grade robotic vacuum cleaner. Such a cleaner can incorporate a reasoning engine that aids in how best to operate. For example, the reasoning engine can observe how much dirt is detected during vacuuming and a time of day during operation. Based on such environmental data, the cleaner can generate a hypothesis on when it would be best to vacuum a room for maximal benefit. Although the previous example is simply, the concepts can be extended to humanoid robots, which can be "trained" to accomplish human tasks. Example humanoid robots that could leverage the inventive subject matter include NASA's Robonaut, or Honda's Asimo robot. Still further, the hypotheses can be used by robots for navigation a in real-world environment and in all three dimensions. Through exploration and experimentation in an environment, the reasoning engine can provide feedback to the robot on how to adapt its view of the world or how to adapt its navigation algorithms. One should appreciate that robotic reasoning engines can function at different levels within the robot; at the whole robot level (e.g., body, etc.), at the extremity level (e.g., arm, leg, head, etc.), at the digit level (e.g., finger, toe, etc.), or even at the "cognitive" level (i.e., internal processing). These approaches can be used by reasoning engines to discover how to map brain waves to desired motions on a robotic prosthetic of a patient.

Search engines can also benefit from application of the disclosed reasoning engine techniques. Rather than merely providing search results back to a user, search engines can be configured to return a reason why a result set is constructed or returned. Therefore, the inventive subject matter is considered to include adapting existing search engine to provide reasoning services to users.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A computer-based relational reasoning engine comprising:
   an inquiry interface configured to receive an inquiry over a network;
   a database containing relational knowledge and configured to store data objects, wherein each one of the data objects has data object attributes; and
   at least one server coupled with the inquiry interface and that is, upon execution of software instructions stored in a non-transitory computer readable memory by at least one processor, configurable to:
      receive, via the inquiry interface, the inquiry, wherein the inquiry relates to a relationship between objects of a set of objects;
      search the database for data objects related to objects in the set of objects;
      select one or more reasoning rules sets from a plurality of reasoning rules sets as a function of data object attributes of the data objects related to objects in the set of objects;
      generate a plurality of hypotheses with respect to relations between at least one pair of objects of the set of objects as a function of the one or more reasoning rules sets related to the data object attributes of the data objects related to the objects in the set of objects and as a function of an inference with respect to relations between the set of data objects; and
      configure a computing device to present a response to the inquiry, wherein the response is based on at least one hypothesis of the plurality of hypotheses.

2. The engine of claim 1, wherein the at least one hypothesis relates to a physical relationship between the at least one pair of objects in the set of objects.

3. The engine of claim 1, wherein the at least one hypothesis relates to a behavior of the set of objects over time.

4. The engine of claim 1, wherein the at least one hypothesis relates to a behavior of a moving object over time.

5. The engine of claim 1, wherein the at least one hypothesis relates to a relative position of one object of the set of objects with respect to another object of the set of objects.

6. The engine of claim 1, wherein the at least one hypothesis relates to a relationship between different mental representations.

7. The engine of claim 1, wherein the at least one hypothesis is based on a context of an environment.

8. The engine of claim 1, wherein the at least one hypothesis relates to a derived relationship.

9. The engine of claim 1, wherein the plurality of hypotheses is generated based on a priori knowledge.

10. The engine of claim 1, wherein the plurality of hypotheses is generated based on a previously generated hypothesis.

11. The engine of claim 1, wherein the set of objects comprises one or more physical objects, virtual objects, or 3D-rendered objects.

12. The engine of claim 1, wherein the set of objects comprises a moving object.

13. The engine of claim 1, wherein the set of objects comprises one or more events.

14. The engine of claim 1, wherein the inquiry comprises a relational attribute.

15. The engine of claim 1, wherein the inquiry comprises at least one relational attribute and at least one non-relational attribute.

16. The engine of claim 1, wherein the inquiry comprises at least one of text data, audio data, image data, video data, and sensor data.

17. The engine of claim 1, wherein the at least one server comprises a cloud-based service.

18. The engine of claim 1, wherein the at least one server is further configurable to request, via the inquiry interface, updated data associated with the plurality of hypotheses and according to a validation plan.

19. The engine of claim 1, wherein the at least one server is further configurable to change the plurality of hypotheses as a function of updates to the related data objects.

20. The engine of claim 1, wherein the inquiry interface comprises a mobile device interface.

21. The engine of claim 20, wherein the mobile device interface comprises at least one of a mobile phone, a portable computer, and a computing tablet.

22. The engine of claim 1, wherein the data objects include at least one of visual data, text-based data, video data, identity data, demographic data, and sensor data.

23. The engine of claim 1, wherein the data objects comprise an observed change in an object of a set of objects.

24. The engine of claim 1, wherein the presentation includes reasons or additional information supporting the at least one hypothesis.

25. The engine of claim 24, wherein the reasons include a type of reasoning or reason steps supporting the at least one hypothesis.

26. The engine of claim 25, wherein the type of reasoning includes at least one of deductive reasoning, adductive reasoning, inductive reasoning, amplitative reasoning, case-based reasoning, metaphorical mapping, forward chaining reasoning, backward chaining reasoning, analogical reasoning, cause-and-effect reasoning, defeasible or indefeasible reasoning, comparative reasoning, conditional reasoning, decompositional reasoning, exemplar reasoning, modal logic, set-base reasoning, systemic reasoning, syllogistic reasoning, probabilistic reasoning, and paraconsistent reasoning.

27. The engine of claim 1, wherein the presentation comprises a web page within a browser operating on the computing device.

28. The engine of claim 1, wherein the at least one server generates the plurality of hypotheses in real-time relative to changes in the data objects.

\* \* \* \* \*